(12) United States Patent
Srisathapat et al.

(10) Patent No.: US 8,460,244 B2
(45) Date of Patent: Jun. 11, 2013

(54) RESERVOIR COMPARTMENT ADAPTER FOR INFUSION DEVICE

(75) Inventors: Chad Srisathapat, Sun Valley, CA (US); Afshin Bazargan, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 441 days.

(21) Appl. No.: 12/346,757

(22) Filed: Dec. 30, 2008

(65) Prior Publication Data

US 2010/0168670 A1    Jul. 1, 2010

(51) Int. Cl.
*A61M 37/00* (2006.01)
*A61M 31/00* (2006.01)
*A61M 5/00* (2006.01)

(52) U.S. Cl.
USPC .......................... 604/131; 604/93.01; 604/232

(58) Field of Classification Search
USPC ................... 604/111, 232, 228, 72, 118, 121, 604/131, 187, 191, 208, 218, 234, 235, 93.01
See application file for complete search history.

(56) References Cited

U.S. PATENT DOCUMENTS

| 4,351,335 A | 9/1982 | Whitney et al. |
| 2003/0120212 A1 | 6/2003 | Dedig et al. |

FOREIGN PATENT DOCUMENTS

| WO | 0025844 A1 | 5/2000 |
| WO | 2006132146 A1 | 12/2006 |
| WO | 2009043564 A1 | 4/2009 |

OTHER PUBLICATIONS

PCT Search Report and Written Opinion for PCT/US2009/068669.

*Primary Examiner* — Nicholas Lucchesi
*Assistant Examiner* — Brooke Matney
(74) *Attorney, Agent, or Firm* — Medtronic MiniMed, Inc.

(57) ABSTRACT

The present invention provides a reservoir compartment adapter for use with a fluid delivery device. The adapter includes a first end adapted for coupling with a fluid delivery device, a second end adapted for coupling with a connector, and a structure between the first end and the second end including an interior space for receiving the reservoir, wherein an extended reservoir compartment for accommodating the reservoir is adapted to be formed when the first end is coupled to the fluid delivery device, and the reservoir is adapted to be secured in the extended reservoir compartment when the connector is coupled to the second end. The adapter allows a user of a delivery device accommodating reservoirs of a certain size to manage periods where increased medication dosage is needed without the burden of carrying a larger delivery device for accommodating reservoirs filled with the increased dosage.

26 Claims, 3 Drawing Sheets

RESERVOIR COMPARTMENT ADAPTER FOR INFUSION DEVICE

FIELD OF THE INVENTION

The present invention relates to an apparatus for extending a reservoir compartment of an infusion device to accommodate reservoirs of different sizes.

BACKGROUND OF THE INVENTION

Infusion devices and systems have become relatively prevalent in the medical field for use in delivering or dispensing prescribed medication such as insulin to a patient. In one form, such devices comprise a transportable, pocket-size pump housing capable of receiving a reservoir of medication for administration to the patient through an associated catheter or infusion set.

Infusion devices have significant advantages over traditional medication delivery methods because of their precision, consistency, and versatility. Patients are able to set exact dosage amounts and generally benefit from receiving medication from pumps during physical activity or other occasions that would otherwise not easily be suited for doing so. As a result, infusion pumps have effectively reduced the restrictions that a diabetic patient's medical needs place upon him allowing the patient to live a more active and fulfilling lifestyle.

Generally, medication reservoirs have been used with the infusion devices to invasively deliver medication to the patient. According to the patient's needs, the medication reservoirs are available in various sizes in order to hold various amounts of medication or fluid. Typically, the medication reservoir is operatively inserted in, or attached to, the infusion device. A plunger is then actuated to force medication out of the reservoir, and deliver the medication via a tube to an insertion set on the patient.

A problem associated with a typical infusion device is that the device can only accommodate one reservoir size because a reservoir compartment in the infusion device has fixed dimensions (i.e. length, width, height, diameter, etc.). To administer medication contained in reservoirs of different sizes, a plurality of infusion devices are required to respectively accommodate the different-sized reservoirs. Hence, a patient having access to only one infusion device is limited to only using reservoirs of one size.

Accordingly, what is needed is an apparatus and method for facilitating a single infusion device to accommodate reservoirs of varying sizes. Doing so would eliminate the need for multiple devices when administering medication from different-sized reservoirs is desired.

SUMMARY OF THE INVENTION

Embodiments of the present invention are directed to a reservoir compartment adapter for extending a reservoir compartment of a fluid delivery device to receive a larger reservoir. The compartment adapter allows a user of a delivery device accommodating reservoirs of a certain size to manage periods where increased medication dosage is needed without the burden of carrying a larger delivery device for accommodating reservoirs filled with the increased dosage.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the present invention is embodied in a reservoir compartment adapter for use with a fluid delivery device. The adapter comprises a first end for coupling with a reservoir compartment of the device, the reservoir compartment including a first interior space for housing a reservoir, a second end for coupling with a locking cap, and a stepped cylindrical structure including a second interior space for receiving the reservoir. An extended housing combining the first interior space and second interior space for accommodating the reservoir is formed when the first end is coupled to the reservoir compartment. The reservoir is operatively connected to the device by inserting the reservoir in the extended housing and securing the reservoir therein by coupling the locking cap to the second end while the locking cap interfaces an end of the reservoir.

The first end comprises male threads formed on an exterior diameter of the first end for mating with female threads formed on an interior diameter of the reservoir compartment. Moreover, the second end comprises female threads formed on an interior diameter of the second end for mating with male threads formed on an exterior diameter of the locking cap. Also, the locking cap may be a fluid conduit between the reservoir and infusion tubing for delivering fluid contained in the reservoir through the infusion tubing. In one embodiment, the reservoir is sized to hold 3.0 mL of fluid.

In another embodiment, a system for operatively connecting a reservoir in a fluid delivery device comprises a fluid delivery device including a reservoir compartment, the reservoir compartment including a first interior space for housing a reservoir, a locking cap for securing the reservoir within the device, and a reservoir compartment adapter including a first end for coupling with the reservoir compartment, a second end for coupling with the locking cap, and a stepped cylindrical structure including a second interior space for receiving the reservoir, An extended housing combining the first interior space and second interior space for accommodating the reservoir is formed when the first end of the adapter is coupled to the reservoir compartment. The reservoir is operatively connected to the device by inserting the reservoir in the extended housing and securing the reservoir therein by coupling the locking cap to the second end of the adapter while the locking cap interfaces and end of the reservoir.

In one embodiment, the device comprises a detector for detecting the adapter coupled to the reservoir compartment. For example, the detector may be at least one a magnetic sensor, an optical sensor, a mechanical switch, and a color sensor. The device may also comprise control circuitry for modifying operation of the device when the adapter is detected to be coupled to the reservoir compartment.

In a further embodiment, a fluid delivery device comprises a reservoir compartment for housing a reservoir, control circuitry for operating the device, and a detector for detecting a reservoir compartment adapter coupled to the reservoir compartment.

In another embodiment, a method for operatively connecting a reservoir in a fluid delivery device comprises coupling a first end of a reservoir compartment adapter to a reservoir compartment of a fluid delivery device, wherein the reservoir compartment includes a first interior space for housing a reservoir, and the adapter comprises a stepped cylindrical structure including a second interior space for receiving the reservoir, forming an extended housing combining the first interior space and second interior space for accommodating the reservoir when the first end of the adapter is coupled to the reservoir compartment, and operatively connecting the reservoir to the device by inserting the reservoir in the extended housing and securing the reservoir therein by coupling a locking cap to a second end of the adapter while the locking cap interfaces and end of the reservoir.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. Features, elements, and aspects of the invention that are referenced by the same numerals in different figures represent the same, equivalent, or similar features, elements, or aspects in accordance with one or more embodiments.

DETAILED DESCRIPTION OF THE PREFERRED EMBODIMENTS

Figure 1:
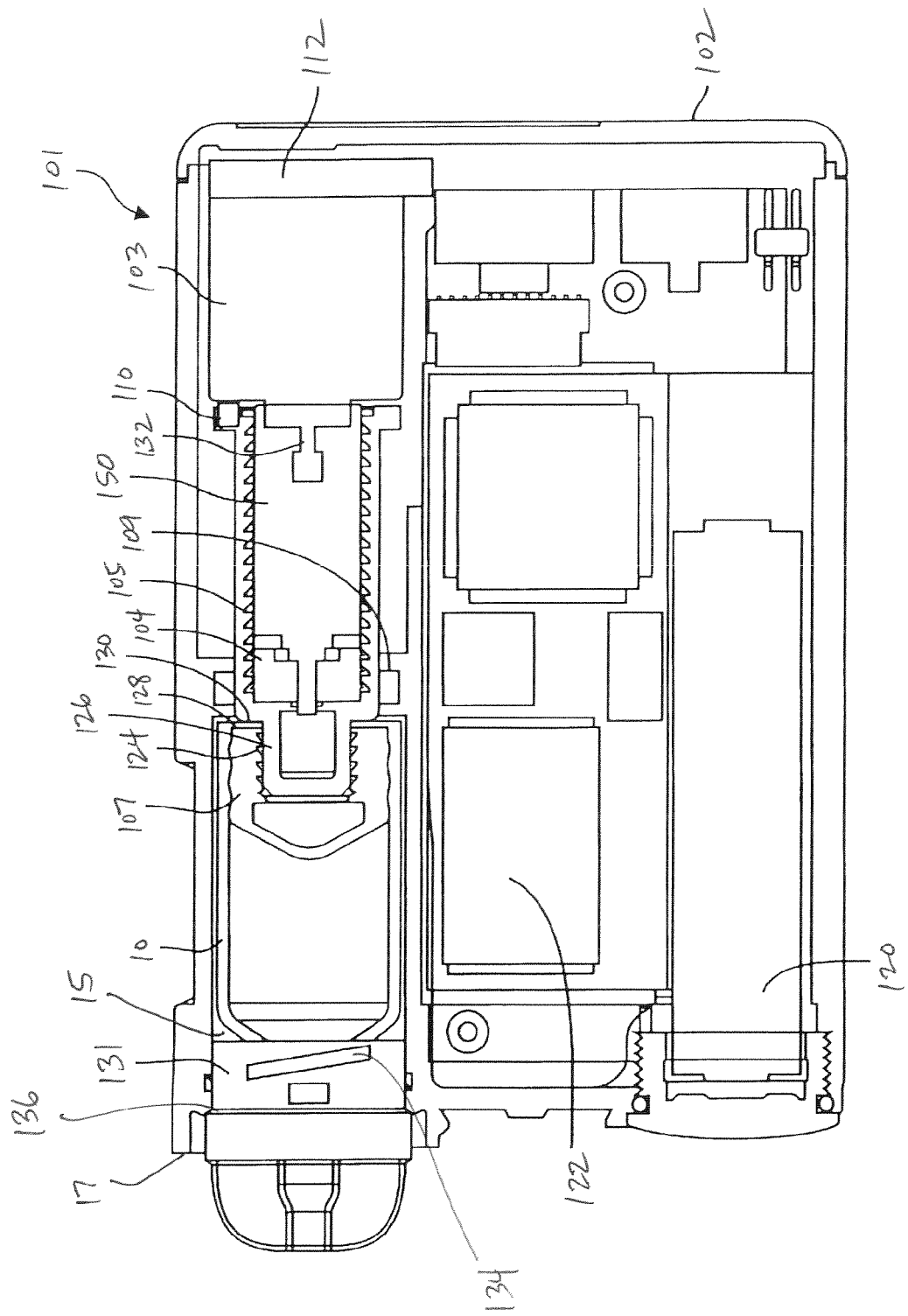
FIG. 1 illustrates a side plan, cut-away view of a fluid delivery device in accordance with an embodiment of the invention.

Embodiments of the present invention relate to a reservoir compartment adapter for use with a fluid delivery device. As shown in the drawings for purposes of illustration, embodiments of the invention include a reservoir compartment adapter for an infusion device. In particular embodiments, the reservoir compartment adapter is used in conjunction with a medication delivery device for delivering medication, such as insulin, contained in the reservoir to a patient. In further embodiments, the fluid delivery device may be used to deliver medical substances, such as vitamins, hormones, vaccines, antibiotics or other medications, or other liquid substances, such as dyes, tracers or the like, to the patient. The reservoir compartment adapter allows fluid reservoirs having different sizes to be operatively coupled to the delivery device. Accordingly, a single delivery device may be used when fluid from reservoirs having different sizes is to be administered to a patient.

Embodiments of the present invention may be implemented in an infusion device including an in-line drive system of the type described in U.S. Pat. Nos. 6,248,093; 6,362,591; and 6,555,986, all of which are specifically incorporated by reference herein. Other embodiments of the present invention may be implemented in an infusion device that receives data from a sensor inserted into a patient's body as generally described in U.S. patent application Ser. No. 10/867,529 entitled "System for Providing Blood Glucose Measurements to an Infusion Device" and filed on Oct. 14, 2004, which is incorporated by reference. In further embodiments, the infusion device may be any other type of external infusion pump that facilitates the delivery of fluid into the body.

An infusion device according to the present invention may include a housing to enclose a drive system, a fluid containment assembly, and a power supply. The device's drive system generally includes a small motor (DC, stepper, solenoid, piezoelectric, piston drive, peristaltic pump, shape memory alloy driven, or other type) and drive train components such as gears, screws and levers that act in concert to convert rotational motor motion to translational displacement of a piston in a fluid reservoir. In some embodiments, the drive system may use gas or other types of pressure systems that induce displacement of the piston in the fluid reservoir. The fluid containment assembly may include the reservoir, flexible tubing and a catheter or infusion set that transports the fluid or medication from the infusion device to the body of the user. The device's electronic system may include programmable controls for regulating the motor, as well as for setting desired dosage intervals over a certain period of time.

FIG. 1 illustrates a side plan, cut-away view of a fluid delivery device according to an embodiment of the invention. Notably, other types of fluid delivery devices may also be used with the reservoir compartment adapter in accordance with embodiments of the present invention. Referring to FIG. 1, a device 101, containing a lower section 102 for a power supply 120 and electronic control circuitry (microprocessor) 122, accommodates a driving device, such as a motor 103 (e.g., a solenoid, stepper or DC motor), a first drive member, such as an externally threaded drive gear or screw 104, a second drive member, such as an internally threaded plunger gear or slide 105, and a removable reservoir 10. The reservoir 10 may include a piston 107 with O-rings or integral raised ridges for forming a water and air tight seal. The reservoir 10 is secured into a reservoir compartment 15 with a connector cap 131. The connector 131 also serves as an interface between the reservoir 10 and a conduit for delivering fluid to the patient, such as tubing and an infusion set (not shown) adhered to the patient. In particular embodiments, the reservoir piston 107 is coupled to a plunger slide 105 by a releasable coupler. In the illustrated embodiment, the coupler includes a female portion 124 which receives a male portion 126 carried by the plunger slide 105. The female portion 124 is positioned at the end face 128 of the piston 107 and includes a threaded cavity which engages the threads of a male screw extending from the end 130 of the plunger slide 105.

While particular embodiments of the present invention are directed to disposable, pre-filled reservoirs 10, alternative embodiments may use user-filled, refillable, refurbished, or the like reservoirs 10. The reservoir 10 can be pre-filled with insulin (or other drug or fluid) and inserted into the fluid delivery device 101. Alternatively, the reservoir 10 may be filled by the patient using an adapter handle (not shown) attached to the piston 107 on the reservoir 10. After the reservoir 10 is filled, the handle is removed (such as by unscrewing the handle) so that the reservoir 10 can be placed into the fluid delivery device 101.

Referring to FIG. 1, as the drive shaft 132 of the motor 103 rotates, the drive screw 104 drives the plunger slide 105 directly to obtain the axial displacement against the reservoir piston 107 to deliver the predetermined amount of medication or fluid. A conventional gear box 150 couples the drive screw 104 to the drive shaft 132 of the motor 103. When using a DC or stepper motor, the motor can be rapidly rewound when the reservoir is emptied or as programmed by the user. A sealing device, such as an O-ring seal 109, is in contact with the plunger slide 105 thus allowing it to move axially while maintaining a water resistant barrier between the cavity holding the reservoir 10 and the motor 103. This prevents fluids and other contaminants from entering the drive system.

An anti-rotation key 110 is affixed to the plunger slide 105 and is sized to fit within a groove (not shown) axially disposed in the device 101. This arrangement serves to prevent motor and plunger slide rotation which might otherwise result from the torque generated by the motor 103 in the event that the friction of the O-ring seal 109 is not sufficient alone to prevent rotation.

The motor 103 is a conventional motor, such as a DC or stepper motor, and is journal mounted in the device 101 by a system compliance mounting 112. A system compliance mount can be useful in aiding motor startup. The compliance mounting 112 can include a rubberized mounting bracket. Alternatively, the mounting 112 could be accomplished using a shaft bearing and leaf spring or other known compliance mountings.

The reservoir 10 is coupled to the connector 131 and then inserted into the reservoir compartment 15 of the device 101 and secured to the device 101 using the connector 131. The connector 131 may be of the type described in U.S. Pat. No. 6,585,695, which is incorporated by reference herein. The connector 131 is used to secure the reservoir 10 within the reservoir compartment 15 and to connect the reservoir to a conduit through which the fluid or medication can be delivered, such as tubing and an infusion set (not shown). Alternatively, the reservoir 10 may be inserted into and secured within the reservoir compartment 15 using another type of cap and then connected through an opening in the cap to a conduit using another type of connector, such as a standard Luer-type connector.

As shown in FIG. 1, the reservoir 10 is of a predetermined size in order to operatively fit into the compartment 15. For example, the reservoir 10 may be sized to hold up to approximately 1.6 mL of fluid or medication, although in alternative embodiments, the reservoir 10 may be sized to hold other amounts of fluid or medication. Accordingly, if the reservoir 10 is sized to hold 1.6 mL, then component dimensions of the device 101 are sized such that when the 1.6 mL reservoir is operatively coupled to a driving means of the device 101 and accommodated in the compartment 15, the connector 131 can mate with an outlet end 17 of the compartment 15 to secure the reservoir 10 in the device 101.

In particular embodiments, the outlet end 17 may be specifically configured to mate with the connector 131. For example, an interior diameter of the outlet end 17 includes female threads (not shown) that engage male threads 134 on an exterior diameter of the connector 131. Once the connector 131 is mated with the outlet end 17, the device 101 is water resistant, preventing fluid from entering the compartment 15. Moreover, the connector 131 acts as an interface between the reservoir 10 and a conduit such as tubing and an infusion set (not shown) adhered to the patient.

In particular embodiments, the connector 131 may include one or more detents (not shown) that extend radially from the exterior of the connector 131 and are adapted to engage into detent openings or recesses (not shown) in the housing of the device 101. In other embodiments, a shoulder 136 may be formed as part of the connector 131 and is adapted to seat against the housing of the device 101 to form a watertight seal. This prevents any water from entering the housing of the device 101. Further aiding in the watertight construction is an O-ring seal (not shown) which is disposed in the housing of the device 101 and located just above the shoulder (not shown). Such exemplary features of the connector 131 are further described in U.S. Pat. No. 6,585,695, which is incorporated by reference.

Depending on implementation, reservoirs having a size smaller than the predetermined size may be used with the delivery device of the present invention. For example, reservoirs sized to hold less than 1.6 mL of fluid may also be operatively coupled to the driving means of the device 101, accommodated in the compartment 15 and secured therein when the connector 131 is attached to the outlet end 17 of the compartment 15. However, in the embodiment shown in FIG. 1, a reservoir having a length longer than the predetermined size (e.g. a reservoir sized to hold more than 1.6 mL of fluid) may not be operatively accommodated in the compartment 15 because the additional length of the reservoir housed in the compartment may prevent the connector 131 from coupling with the outlet end 17.

Figure 2:
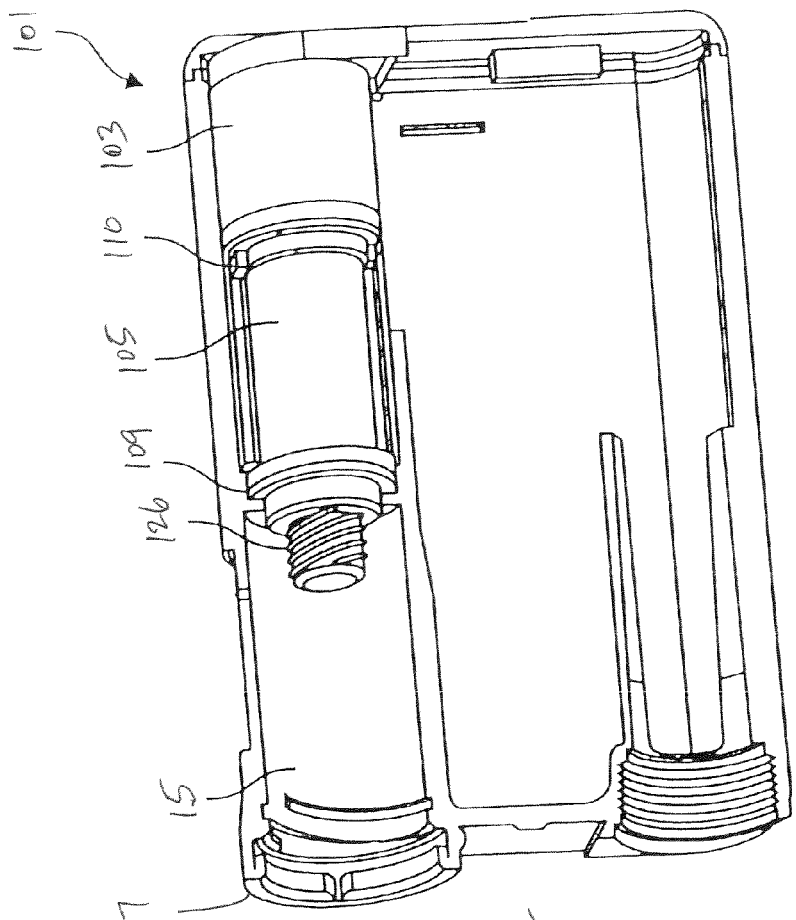
FIG. 2 illustrates a reservoir compartment adapter for use with a fluid delivery device in accordance with an embodiment of the invention.
Figure 2:
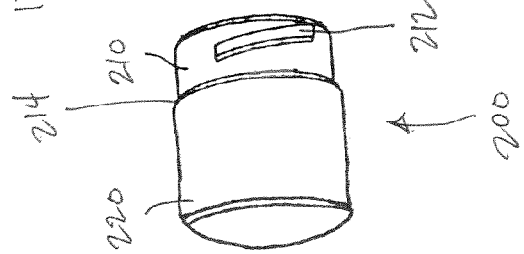
Figure 2:
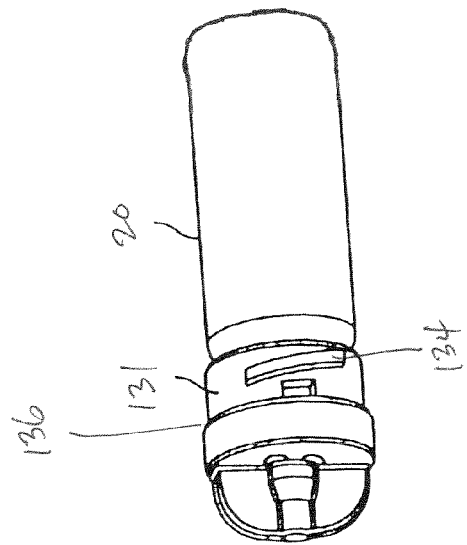
Figure 3:
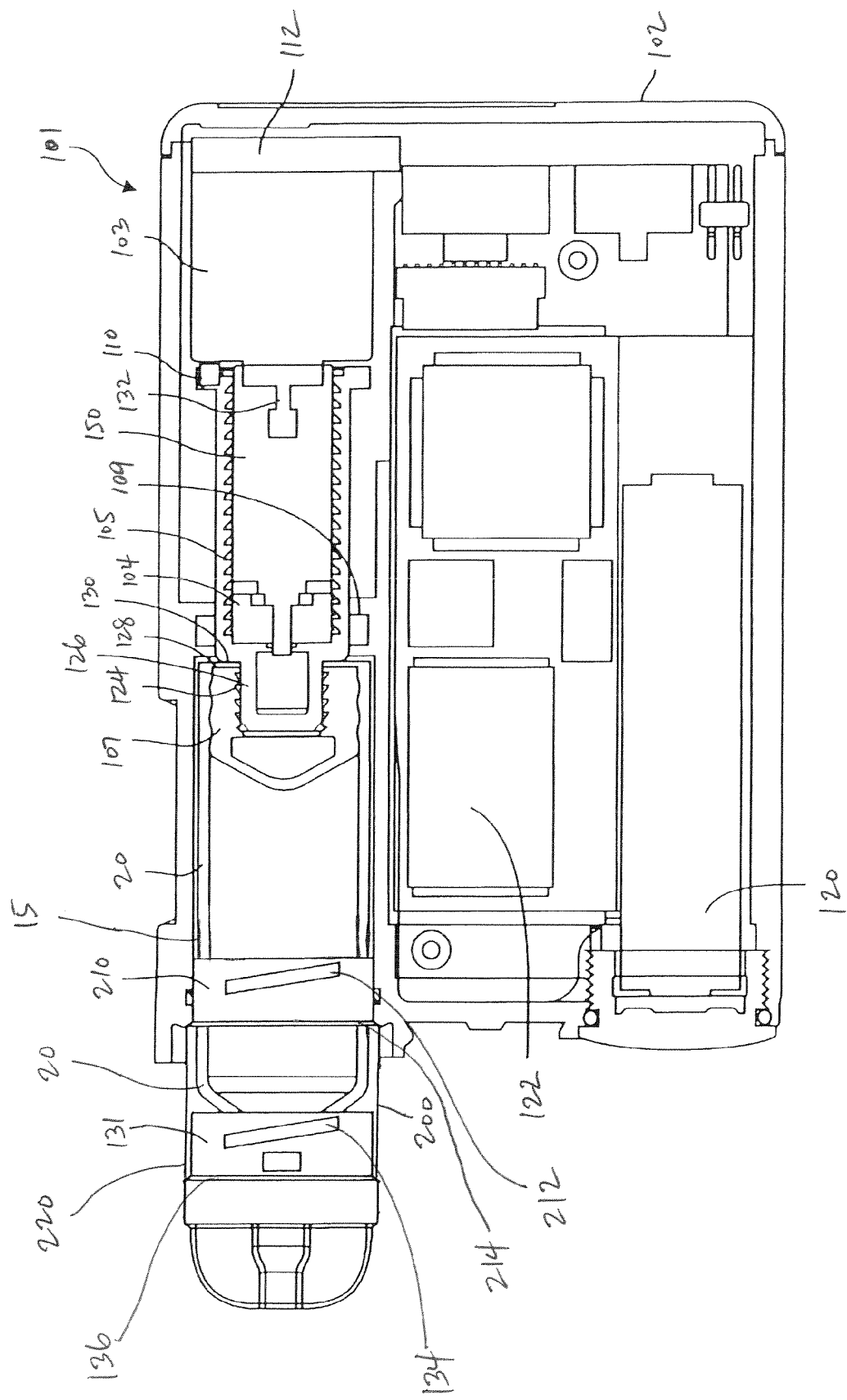
FIG. 3 illustrates a side plan, cut-away view of a reservoir compartment adapter operatively connected to a fluid delivery device in accordance with an embodiment of the invention.

FIG. 2 illustrates a reservoir compartment adapter for use with an exemplary fluid delivery device according to an embodiment of the invention. FIG. 3 illustrates a reservoir compartment adapter operatively coupled to an exemplary fluid delivery device according to an embodiment of the invention.

Referring to FIGS. 2 and 3, a reservoir compartment adapter 200 is used with the delivery device 101 to facilitate use of a reservoir 20 with the device 101. In the illustrated embodiment, the reservoir 20 is sized to hold more fluid than the reservoir 10 shown in FIG. 1, and therefore has a longer length than the reservoir 10. For example, the reservoir 20 may be sized to hold up to approximately 3.0 mL of fluid or medication, but in alternative embodiments, the reservoir 20 may be sized to hold other amounts of fluid. Although the reservoir 10 of FIG. 1 and the reservoir 20 of FIG. 2 differ in size, the dimensions of the device 101 in both FIGS. 1 and 2, and specifically the size of the compartment 15, are the same.

In particular embodiments, the adapter 200 is made of a suitable plastic material. However, in alternative embodiments, the adapter 200 may be made out of other materials, such as composites, metals, ceramics, Topas®, or the like. In the embodiment illustrated in FIG. 2, the adapter 200 has a generally stepped cylindrical structure. An interior diameter of the adapter 200 is large enough to allow a diameter of the reservoir 20 to pass within the adapter 200. Moreover, when the adapter 200 is connected to the outlet end 17, a length of the compartment 15 combines with a length of the adapter 200 in order to house the longer reservoir 20. Hence, a length of the adapter 200 is sufficiently long to house a portion of the reservoir 20 protruding out of the outlet end 17 when the reservoir 20 is inserted in the compartment 15.

The adapter 200 is configured to mate with the outlet end 17 of the compartment 15. In particular embodiments, an exterior diameter of a first end 210 of the adapter 200 may include male threads 212 that engage with female threads (not shown) located on the interior diameter of the outlet end 17. In other embodiments, the first end 210 may include one or more detents (not shown) that extend radially from the exterior of the first end 210 and are adapted to engage into detent openings or recesses (not shown) in the housing of the device 101. This engagement may result in a "click" when the first end 210 is appropriately seated, thus providing both tactile and audible feedback to the user that the first end 210 is securely engaged in the housing of the device 101. Moreover, the detents aligning with the recesses may serve as a visual indicator that the first end 210 is appropriately seated. In further embodiments, a shoulder 214 may be formed as part of the first end 210 and be adapted to seat against the housing of the device 101 to form a watertight seal. An O-ring seal (not shown) may also be disposed in the housing of the device 101 and located just above the shoulder (not shown). In yet other embodiments, the first end 210 may be mated to the outlet end 17 using other coupling means, such as latches or locks. Accordingly, the adapter 200 may be connected directly to the compartment 15 by mating the first end 210 to the outlet end 17. When the first end 210 is mated to the outlet end 17, a watertight seal is created, thus preventing fluid from entering the device 101 at the connection point between the first end 210 and the outlet end 17.

A second end 220 of the adapter 200 is configured to mate with a connector 131. In FIG. 2, the connector 131 is shown attached to an end of the reservoir 20. The reservoir 20 is coupled to the connector 131 and then inserted into and secured to the device 101 using the connector 131. In particular embodiments, an interior diameter of the second end 220 may include female threads (not shown) that engage with male threads 134 located on the exterior diameter of the connector 131. In other embodiments, the connector 131 may include one or more detents (not shown) that extend radially from the exterior of the connector 131 and are adapted to engage into detent openings or recesses (not shown) in the second end 220. This engagement may result in a "click" when the connector 131 is appropriately seated, thus providing both tactile and audible feedback to the user that the connector 131 is securely engaged in the second end 220. Moreover, the detents aligning with the recesses may serve as a visual indicator that the connector 131 is appropriately seated. In further embodiments, a shoulder 136 may be formed as part of the connector 131 and be adapted to seat against the second end 220 to form a watertight seal. An O-ring seal (not shown) may also be disposed on the second end 220 and located just above the shoulder (not shown). In yet other embodiments, the second end 220 may be mated to the connector 131 using other coupling means, such as latches or locks.

Referring to FIG. 3, the reservoir 20 is operatively coupled to the device 101 by inserting the reservoir 20 into a combined interior space of the adapter 200 and reservoir compartment 15 of the device 101, and securing the reservoir 20 therein by mating the connector 131 with the second end 220. Once the connector 131 is mated, fluid is prevented from entering the combined interior space of the compartment 15 and adapter 200. Moreover, as with other embodiments, the connector 131 acts as an interface between the reservoir 20 and a conduit such as tubing and an infusion set (not shown) adhered to the patient. In alternative embodiments, the reservoir 20 may be inserted into and secured within the combined interior space of the adapter 200 and reservoir compartment 15 of the device 101 using another type of cap that mates with the second end 220, and then connected through an opening in the cap to a conduit using another type of connector, such as a standard Luer-type connector.

In particular embodiments, the delivery device 101 of the present invention is capable of accommodating reservoirs of different sizes using the reservoir compartment adapter 200. For example, the device 101 may accommodate both the reservoir 10 of FIG. 1 and the reservoir 20 of FIGS. 2 and 3. As shown in FIG. 1, the reservoir 10 is operatively coupled to the device 101 when the reservoir 10 is inserted into the compartment 15 and secured therein by mating the connector 131 with the outlet end 17 of the compartment 15. In this embodiment, the reservoir compartment adapter 200 is not needed.

As shown in FIGS. 2 and 3, the reservoir 20 is operatively coupled to the same device 101 using the reservoir compartment adapter 200. Specifically, to accommodate the longer length of the reservoir 20, the adapter 200 is first mated to the outlet end 17 to extend a housing of the compartment 15 past the outlet 17. Thereafter, with the reservoir 20 coupled to the connector 131, the reservoir 20 may be operatively housed in the device 101 by inserting the reservoir 20 through the adapter 200 and into the compartment 15. The reservoir 20 may then be secured to the device 101 by mating the connector 131 with the second end 220 of the adapter 200. Hence, the additional length of the reservoir 20 does not prevent the reservoir from being used with the device 101 because the connected adapter 200 provides an extended housing for the longer reservoir and a mating structure for the connector 131 to mate with in order to secure the reservoir 20 in the device 101. Accordingly, use of the adapter 200 is advantageous because a patient is provided with a choice of different-sized reservoirs, such as a 1.6 mL reservoir and a 3.0 mL reservoir, for use with a single delivery device. For example, while using a delivery device such as an insulin infusion pump, many patients utilize a 1.6 mL reservoir with the pump because it holds a sufficient amount of insulin for such patients. However, some patients require more insulin, and thus utilize a 3.0 mL reservoir with the pump. By using the reservoir compartment adapter with the pump, patients requiring a 3.0 mL reservoir are able to use the same pump as patients requiring a 1.6 mL reservoir, thus eliminating the need to manufacture and use two separate delivery devices to accommodate two different-sized reservoirs. Additionally, a pump that accommodates a 1.6 mL reservoir is typically smaller in size than a pump that accommodates a 3.0 mL reservoir, and the smaller pump is more desirable to patients. Further, if a patient's insulin needs ever increase from a 1.6 mL reservoir to a 3.0 mL reservoir, the patient is able to use the same pump.

In particular embodiments, the device 101 comprises a mechanism for detecting when the reservoir compartment adapter 200 is attached and informing the control circuitry 122 of the attachment. The control circuitry 122 may require such information in order to modify control algorithms for delivering medication to the patient according to a size of an inserted reservoir. For example, a device may have to modify pumping parameters when a different-sized reservoir is accommodated in the device. Also, the algorithm for determining the amount of fluid remaining in the reservoir may be modified when a different-sized reservoir is inserted into the device. In particular embodiments, attachment of the adapter 200 may be detected using a magnetic sensor, an optical sensor, a mechanical switch, or a color sensor, for example.

In some embodiments, the mechanism for detecting when the adapter 200 is attached to the device 101 is on the adapter 200 and/or on the device 101. In one embodiment, the device 101 may include one or more mechanical switches that are manipulated by the adapter 200 when the adapter 200 is attached to the device 101 to inform the control circuitry 122 of the attachment. In another embodiment, the adapter 200 may include one or more contacts that mate with corresponding contacts on the device 101. In an additional embodiment, one or more magnets may be mounted on the adapter 200 to provide information about the attachment to a magnetic sensor housed in the device 101. In a further embodiment, the adapter 200 may include a bar code that provides information about the attachment to an optical scanner in the device 101. In yet another embodiment, the adapter 200 may include a colored band that is detected by a color sensor in the device 101. The bar code or colored band may completely encircle or partially extend around the adapter 200, and may be applied to a surface of the adapter 200 by means of a painted mark, printing, spraying, molding, adhered sticker, or the like.

Alternatively, the mechanism for detecting when the adapter 200 is attached to the device 101 may be on the reservoir itself and/or on the device 101. The above embodiments may be applied to the reservoir itself, rather than the adapter 200, and indicate the reservoir size (i.e., 1.6 mL, 3.0 mL), and the device 101 may determine that the adapter 200 is attached to the device 101 based on the indicated reservoir size. Such a mechanism is described, for example, in U.S. patent application Ser. Nos. 12/346,726 and 12/346,730, both entitled "Color Detection System for Detecting Reservoir Presence and Content in Device" and both filed on Dec. 30, 2008, which are incorporated by reference.

In further alternative embodiments, the mechanism for detecting when the adapter 200 is attached to the device 101 may be omitted, and the patient may simply input the information into the device 101 itself.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, any means-plus-function clauses are intended to cover the structure described herein as performing the recited function and not only structural equivalents but also equivalent structures.

What is claimed is:

1. A reservoir compartment adapter for use with a reservoir containing fluid, a fluid delivery device for delivering the fluid from the reservoir into a body, the fluid delivery device having a reservoir compartment, the reservoir compartment having a first length and including a first interior space for receiving the reservoir, and a connector for coupling with the reservoir, the reservoir compartment adapter having a second length and further comprising:
a first end and a second end, the reservoir compartment adapter including a second interior space for receiving the reservoir, the first end defined to couple with an outlet end of the fluid delivery device, the second end defined to couple with the connector, wherein the second end extends past the outlet end when the first end is removably coupled with the outlet end, and wherein the reservoir compartment adapter is between the connector and the outlet end when the first end is removably coupled with the outlet end and the second end is removably coupled with the connector,
wherein an extended reservoir compartment having a third length is formed by adding the second length to the first length when the first end of the reservoir compartment adapter is removably coupled to the outlet end of the fluid delivery device, wherein the third length is equal to or longer than the reservoir, the extended reservoir compartment being further defined by the first interior space and the second interior space to secure the reservoir entirely within the extended reservoir compartment when the connector is coupled to the second end, the reservoir being removable from the extended reservoir compartment without uncoupling the first end from the fluid delivery device.

2. The adapter of claim 1, wherein the first end comprises a first thread member for mating with a second thread member formed on the fluid delivery device.

3. The adapter of claim 2, wherein the first end comprises male threads formed on an exterior diameter of the first end for mating with female threads formed on an interior diameter of the reservoir compartment.

4. The adapter of claim 1, wherein the second end comprises a first thread member for mating with a second thread member formed on the connector.

5. The adapter of claim 4, wherein the second end comprises female threads formed on an interior diameter of the second end for mating with male threads formed on an exterior diameter of the connector.

6. The adapter of claim 1, wherein the first end comprises one or more detents that extend radially from the exterior of the first end and are adapted to engage into detent openings in the fluid delivery device.

7. The adapter of claim 1, wherein the first end comprises a shoulder seated against a housing or existing seal of the fluid delivery device to form a watertight seal.

8. The adapter of claim 1, wherein the connector is an interface between the reservoir and a conduit for delivering the fluid from the reservoir into the body.

9. The adapter of claim 1, wherein the reservoir is sized to hold approximately 3.0 mL of fluid when the adapter is coupled to the fluid delivery device.

10. The adapter of claim 1, wherein the reservoir is longer than the first length and extends past the outlet end.

11. The adapter of claim 1, wherein a diameter of the reservoir can pass within an interior diameter of the adapter.

12. A fluid delivery system for delivering fluid into a body, the system comprising:
a reservoir that contains the fluid;
a fluid delivery device that delivers the fluid from the reservoir into the body, the fluid delivery device including a reservoir compartment having a first length and including a first interior space for receiving the reservoir;
a connector to be coupled to the reservoir; and
a reservoir compartment adapter having a second length and including a second interior space for receiving the reservoir, the reservoir compartment adapter having a first end defined to couple with an outlet end of the fluid delivery device and a second end defined to couple with the connector, wherein the second end extends past the outlet end when the first end is removably coupled with the outlet end, and wherein the reservoir compartment adapter is between the connector and the outlet end when the first end is removably coupled with the outlet end and the second end is removably coupled with the connector,
wherein an extended reservoir compartment having a third length is formed by adding the second length to the first length when the first end of the reservoir compartment adapter is removably coupled to the outlet end of the fluid delivery device, wherein the third length is equal to or longer than the reservoir, the extended reservoir compartment being further defined by the first interior space and the second interior space to entirely contain the reservoir when the connector is coupled to the second end of the reservoir compartment adapter, the reservoir being removable from the extended reservoir compartment without uncoupling the first end of the reservoir compartment adapter from the fluid delivery device.

13. The system of claim 12, wherein the first end comprises a first thread member for mating with a second thread member formed on the fluid delivery device.

14. The system of claim 13, wherein the first end comprises male threads formed on an exterior diameter of the first end for mating with female threads formed on an interior diameter of the reservoir compartment.

15. The system of claim 12, wherein the second end comprises a first thread member for mating with a second thread member formed on the connector.

16. The system of claim 15, wherein the second end comprises female threads formed on an interior diameter of the second end for mating with male threads formed on an exterior diameter of the connector.

17. The system of claim 12, wherein the first end of the reservoir compartment adapter comprises one or more detents that extend radially from the exterior of the first end and are adapted to engage into detent openings in the fluid delivery device.

18. The adapter of claim 12, wherein the first end of the reservoir compartment adapter comprises a shoulder seated against a housing or existing seal of the fluid delivery device to form a watertight seal.

19. The system of claim 12, wherein the connector is an interface between the reservoir and a conduit for delivering the fluid from the reservoir into the body.

20. The system of claim 12, wherein the reservoir is sized to hold approximately 3.0 mL of fluid when the reservoir compartment adapter is coupled to the fluid delivery device.

21. The system of claim 12, further comprising a detection system for detecting that the reservoir compartment adapter is coupled to the fluid delivery device.

22. The system of claim 21, wherein the detection system includes at least one of:
 a magnetic sensor;
 an optical sensor;
 a mechanical switch; and
 a color sensor.

23. The system of claim 21, wherein the reservoir compartment adapter includes at least a portion of the detection system.

24. The system of claim 21, wherein the fluid delivery device includes at least a portion of the detection system.

25. The system of claim 21, wherein the fluid delivery device comprises control circuitry for modifying operation of the device when the adapter is detected to be coupled to the device.

26. The system of claim 25, wherein the control circuitry modifying an algorithm for determining an amount of the fluid remaining in the reservoir.

\* \* \* \* \*